United States Patent
Sodoyer et al.

(10) Patent No.: US 6,599,697 B1
(45) Date of Patent: *Jul. 29, 2003

(54) PROCESS FOR PREPARING A MULTICOMBINATORIAL LIBRARY OF VECTORS FOR EXPRESSING ANTIBODY GENES

(75) Inventors: Regis Sodoyer, Sainte Foy les Lyon (FR); Luc Aujame, Fleurieux sur L'Arbresle (FR); Frederique Geoffroy, Bessenay (FR)

(73) Assignee: Pasteur Merieux Serums et Vaccins, Lyons (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/693,234

(22) PCT Filed: Feb. 2, 1995

(86) PCT No.: PCT/FR95/00127

§ 371 (c)(1), (2), (4) Date: Oct. 4, 1996

(87) PCT Pub. No.: WO95/21914

PCT Pub. Date: Aug. 17, 1995

(30) Foreign Application Priority Data

Feb. 10, 1994 (FR) .............................. 94 01519

(51) Int. Cl.[7] .............................. C12O 1/70; C12O 1/68; C12N 15/00; C07K 16/00
(52) U.S. Cl. .............................. 435/5; 435/6; 435/320.1; 435/69.1; 435/471; 435/477; 435/DIG. 1; 435/DIG. 2; 435/DIG. 3; 435/DIG. 23; 435/DIG. 24; 536/23.1; 530/387.1

(58) Field of Search .................................. 435/7.1, 69.1, 435/320.1, 235.1, 5, 6, 471, 455, 477, 488, DIG. 1, DIG. 2, DIG. 3, DIG. 23, DIG. 24, DIG. 34; 536/23.1; 530/387.1

(56) References Cited

U.S. PATENT DOCUMENTS 4,673,640 A * 6/1987 Backman .................. 435/69.1
6,174,708 B1 * 1/2001 Sodoyer et al. ............ 435/91.1

OTHER PUBLICATIONS

Geoffroy et al., Gene, vol. 151., pp. 109–113.*
Lewin, Benjamin Genes IV Cell Press, Cambridge, Mass. pp. 641–643, 1990.*
Sambrook et al Molecular Cloning, Cold Spring Harbor Press, Cold Spring Harbor, N.Y. pp. 1.5–1.6 and 4.17–4.20, 1989.*
Maniatas T, Fritsch EF, Sambrook J, 1984. Molecular Cloning: a laboratory manual, Cold Spring Harbor: Cold Spring Harbor Laboratory.*
Waterhouse P, et al, (1993) Combinatorial infection and in vivo recombination: a strategy for making large phage antibody repertoires. Nucleic Acids Res. 21:2265–2266.*

* cited by examiner

Primary Examiner—Padmashri Ponnaluri
(74) Attorney, Agent, or Firm—Larson & Taylor PLC

(57) ABSTRACT

On the basis of a first repertoire of genes coding for a population of one of two kinds of polypeptides capable of being combined, particularly an antibody light chain variable region, and at least one gene, and preferably a second repertoire coding for the other kind of polypeptide, particularly an antibody heavy chain variable region, the genes from the first repertoire are inserted into a first vector to form a vector population and the genes from the second repertoire are inserted into a second vector, at least one of said vectors being a recipient for the expression of both genes as polypeptides irreversibly combined with the outer surface of the product of said vector.

4 Claims, 6 Drawing Sheets

```
pACYC+ primer (base 759)  : 5' GGGAATTCCCCTTAATAAGATGATCT 3'
pACYC+ primer (base 759)  : 5'         GGEcoRI
pACYC- primer (base 2808) : 5' GGGAATTCCATTCAACAAAGCCGCCGTC 3'
pACYC- primer (base 2808) : 5'         GGEcoRI
```

FIG. 5

```
              EcoRI       KpnI             SphI
Link- pAC primer : 3' AATTCGAGCTCGGTACCTCTAGAGCATGCGCTTAA 3'
Link+ pAC primer : 5' AATTCGCTCGAGCCATGGAGATCTCGTACGCTTAA 3'
Link- pAC primer : 3'                              EcoRI  5'
Link- pAC primer : 3' AATTCGCSacI                  XbaI  5'
```

FIG. 6

```
Sac-Kpn+ AttB primer : 5' AATTGCCTGCTTTTTTATACTAACTTGGTAC 3'
Sac-Kpn- AttB primer : 3' TCGACGGACGAAAAAATATGATTGAAC     5'
                           SacI comp.         AttB        KpnI
```

FIG. 7

```
Link+ pVL primer : 5' CATGTGCAGATCTTAGCTAGCATGAATTCCAGAGCTCGTCAGTTCTAGAGTTAA
Link- pVL primer : 3' AATTACGTCTAGAATCGATCGTACTTAAGGTCTCGAGCAGTCAAGATCTCAATT
Link- pAC primer : 3'AflIII   BglII    NheI    EcoRI    SacI    XbaI GCGGCCGCAATCGAGGGGGCGGTAC 3'
CGCCGGCGTTAGCTCCCCCCGC    5'
  NotI                 KpnI
```

FIG. 8 pro Lac+ primer (base 973) : 5' CTAGCTAGCTAACACGACAGGTTCCCGAC 3'
                                                    NheI pro Lac- primer (base 803) : 5' CGGAATTCGTAATCATGGTCATAGCT 3'
pACYC- primer (base 2808) : 5' GG EcoRI

FIG. 9 pelB+ pVL primer : 5' AATTCTAAACTAGTCGCCAAGGAGACAGTCATAATGAAATACCTATTG
pelB- pVL primer : 3' AATTGATTTGATCGATCAGCGGTTCCTCTGTCAGTATTACTTTATGGATAAC
Link- pAC primer : 3' EcoRI
CCTACGGCAGCCGCTGGATTGTTATTACTCGCTGCCCAACCAGCAGCCATGGCCGAGCT 3'
GGATGCCGTCGGCGACCTAACAATAATGAGCGACGGGTTGGTCGGTACCGGC 5'
                                              PelB                    SacI

FIG. 10

VL5 primer : 5' CAGTCTGAGCTCACGCAGCCGCCC 3'
Link- pAC primer : 3' ASacI
CL2 primer : 5' CGCCGTCTAGAACTATGAACATTCTGTAGG 3'
Link- pAC primer : 3' XbaI

FIG. 11

Asc+ pAC primer (base 67) : 5' TTGGCGCGCCTAGTAACACGACAGG 3'
Asc+ pAC primer (base 67) : 5' TTGGAscI
Asc- pAC primer (base 40) : 5' TTGGCGCGCCGGTACCAAGTTAGTA 3'
Asc+ pAC primer (base 67) : 5' TTGGAscI

FIG. 12

Asc+ Cm gene primer (base 3441) :  5' TTGGCGCGCCGAGTTATCGAGATTT 3'
                                                    AscI Asc- Cm gene primer (base 4210) :  5' TTGGGCGCGCCATTCATCCGCTTAT 3'
                                                    AscI

FIG. 13

Link+ pVH and Link- pVH primers
5' TGGCCACCGCGGGTGCTCGAGGATACTAGTCAGTCTAGAGAGTTAAGCGGCCGCAATCGAGGGGGGGTAC 3'
3' ACCGGTGGCGCCCACGAGCTCCTATGATCAGTCGATCGATCTCTCAATTCGCCGGCGTTAGCTCCCCCGC 5'
Link- pAC SacII        XhoI      SpeI     NbeI        NotI              KpnI
               SacI

FIG. 14

PelB+ pVH and PelB- pVH primers
5'      GGTGGCGGCCGCAAATTCTATTCAAGGAGACAGTCATAATGAAATACCTATTGCCTACGGC
3' GGCCACCGCCGGCGTTTAAGATAAGTTCCTCTGTCAGTATTACTTTATGGATAACGGATGCCG
       SacII                                  PelB AGCCGCTGGATTGTTATTACTCGCTGCCCAACCAGCCATGGCCCAGGTGAACTGC         3'
TCGGCGACCTAACAATAATGAGCGACGGGTTGGTCGGTACCGGGTCCACTTGACGAGCT     5'
                                                        XhoI

FIG. 15

GIII+ pVH primer (base 2223) :  5' GGACTAGTGGTGGCGGTGGCTCTCCATTCGTTTGTGAAT 3'
GIII+ pVH primer (base 2223) :  5' GGSpeI Adapteur flexible   Gana III
GIII- pVH primer (base 2885) :  5' CTAGCTAGCATAATAACGGAATACCCAAAAG 3'
GIII- pVH primer (base 2885) :  5' CTAGNheI

FIG. 16

VH4f primer    : 5' CAGGTGCAGCTGCTCGAGTCGGG 3'
VH4f primer  : 5' CAGGTGCAGCTGCXhoI
CGIz primer  : 5' GCATGTACTAGTTTGTCACAAGATTTGGG 3'
                          SpeI

FIG. 17

Nhe+ AttP primer (base 27571) : 5' CTAGCTAGCCGGCTAATGCTCTGTTACAG 3'
                                         NheI
Nhe- AttP primer (base 27820) : 5' CTAGCTAGCATCAAATAATGATTTTATTT 3'
                                         NheI

FIG. 18

VH4f primer : 5' CAGGTGCAGCTGCTCGAGTCGGG 3'
                                    XhoI
PCR Amb primer : 5' GCTCTAGACTAACTAGTTTTGTCACAAGATTTG 3'
PCR Amb primer :                GCXbaI  Amb  SpeI

FIG. 19

Kpn+ Pro Cm primer (base 3270) : 5' GGGGTACCGAATAAATACCTGTGA 3'
Kpn+ Pro Cm primer (base 3270) : 5' GGGKpnI
Kpn- Pro Cm primer (base 3440) : 5' GGGGTACCAAAAAATACGCCCGGTA 3'
Kpn+ Pro Cm primer (base 3270) : 5' GGGKpnI

FIG. 20

PROCESS FOR PREPARING A MULTICOMBINATORIAL LIBRARY OF VECTORS FOR EXPRESSING ANTIBODY GENES

This application is a 371 of PCT/FR95/00127 filed Feb. 2, 1995.

Antibody molecules are formed by the association of two heavy (H) chains and two light (L) chains by means of disulphide bridges. The two heavy chains are mutually associated in accordance with a Y-shaped structure and the two light chains respectively associate with the two branches of this structure in such a way that the variable domains of the light chains ($V_L$) and heavy chains ($V_H$) are-situated close to each other. The binding to the antigen results from the properties of the variable parts of the light and heavy chains. A complex system of rearrangement and selection then enables a substantial quantity of antibody which is specific to an antigen to be induced rapidly.

The standard hybridoma technique makes it possible to select clones of hybrid cells which express genes encoding the light and heavy chains of an antibody molecule. This technique requires the fusion of cells of lymphocytic origin, which contain genes directing the formation of antibodies, and of cells which are capable of giving rise to hybridomas which form immortalized cell lines. The cells which carry the genes in question are generally obtained by randomly creating libraries of circulating cells, with or without prior immunization with a specific antigen, and the hybridomas are screened by means of an antigen-antibody reaction after multiplying and culturing the hybridoma clones. This technique is cumbersome, with a limited yield, and the screening is not simple.

Another method, which uses recombinant bacteriophages, has recently been employed. The principles and the various ways of carrying out this method are described, for example, by D. R. Burton, Tiptech—May 1991, vol. 9, 169–175; D. J. Chiswell et al., Tiptech—March 1992, vol. 10, 80–84; H. R. Hoogenboom et al., Rev. Fr. Transfus. Hémobiol., 1993, 36, 19–47 (see, also, Patent Applications PCT WO 92/01047 and 92/20791).

This technique consists in inserting, into a vector, a repertoire of genes for variable regions of antibodies in association with a bacteriophage gene under conditions which enable the gene to be expressed in the form of a fusion protein which is presented at the surface of the phage, thereby exposing the variable regions of the light and heavy variable chains, which are linked by their disulphide bridges in the manner of an antibody Fab fragment, and in selecting the phages directly by means of a rapid separation method employing the immobilized specific antigen, for example by means of immunoaffinity chromatography. The selected phages can, following elution, infect a bacterium and be used directly for production or for repeating selection cycles. This method is particularly powerful since, in theory, it enables very substantial libraries to be created and a library to be screened in an extremely discriminating, efficient and rapid manner. A phage which lends itself particularly well to this method is the filamentous phage fd, in which it is possible to fuse the fragment encoding one of the heavy or light chains of the antibody with the gene for the minor surface protein and to insert the fragment encoding the other chain in such a way that, after the phage has infected bacteria, a population of phages is obtained which carry, at their surface, a fusion protein which presents the heavy and light chains in a configuration which is able to recognize the antigen and which can, therefore, be screened.

In addition to its simplicity, this technique offers great advantages. In association with the preliminary amplification of the library of antibody genes, it is possible to select one phage presenting a specific antibody fragment in a very large population of phages, of the order of $10^7$, which can make it possible to search for human antibody genes without having necessarily to carry out a prior immunization of the donor.

By means of cleavage followed by religation, or by using two separate libraries of genes for light chains and for heavy chains, it is possible to obtain phages linking one light chain and one heavy chain in a random manner.

However, the number of different clones which it is possible to obtain is limited by the yield of the selection and by the degree of efficiency of the bacterial transformation.

A means of increasing the number of successful combinations linking the light chains of a first library to the heavy chains of a second library was described by P. WATERHOUSE et al., Nucleic acids Research, 1993, Vol. 21, No. 9, 2265–2266, enabling up to $10^{12}$ clones to be obtained using a loxP site-specific recombination system which is sensitive to the action of a Cre recombinase. However, the linkage. remains reversible. Furthermore, there is no control over the action of the recombinase and the recombined vectors do not have any selective advantage over the other vectors.

Now, taking into account the yield of the step for selecting recombinant phages which, in reality, only retains a fraction of the phages of interest, it is desirable to obtain the highest possible yields of recombinant vectors with the least possible number of non-recombinant vectors.

An object of the present invention is, therefore, to provide a process for producing multicombinatorial libraries, in particular in the form of phages or phage-mids, from two repertoires of genes, one for light chains and the other for heavy chains, enabling a very high number of clones to be obtained.

Another object of the invention is to provide such a process in which the number of non-recombinant vectors which are present at the end of the process is reduced.

Another object of the invention is to produce recombinants of this nature which have an enhanced stability.

The invention relates to a process for producing multicombinatorial libraries in which, starting from a first repertoire of genes encoding a population of one of two types of polypeptides which are capable of combining with each other, covalently or non-covalently, in particular variable regions of one of the light chain and heavy chain antibody types, and from at least one gene encoding the other type of polypeptide, in particular a variable region of the other type of antibody chain, or preferably from a second repertoire of genes encoding a population of the said other type, the genes of the said first repertoire are introduced into a first vector in order to form a population of vectors carrying the different genes of the said first repertoire, and the said gene of the said other type or the genes of the said second repertoire are introduced into a second vector, at least one of the said vectors, termed recipient, being arranged to receive, by recombination with the other vector, all or part of the said other vector, together with its gene, under conditions enabling the said recipient vector to contain, after recombination, a gene of one of the two types and a gene of the other type and to express the two genes in the form of linked polypeptides which are able to appear on the external surface of the product of the said vector, being maintained there and being linked together in a multimeric manner, or simulating a multimer, characterized in that the said vectors exhibit means enabling the recombination of the two types of chains to be effected in an irreversible manner.

In that which follows, the invention will be described in the application in which the two types of polypeptides are regions, which are at least in part variable, of light and heavy chains of antibodies. However, it will be understood that the invention also applies to other types of polypeptides which are capable of combining with each other, in particular the chains of heterodimeric receptors such as the α and β chains or γ and δ chains of the T-cell receptors.

Particularly advantageously, the vectors, which are preferably circularized, respectively contain the E. coli attB and the λ phage attP specific recombination sites which are arranged in such a manner as to permit recombination under the influence of the associated recombinase or integrase thereby forming, in a single vector resulting from the recombination, stable junction sequences such as attL and attR.

Naturally, it would also be possible to replace these sites by the specific recombination sites of other bacterium/phage, or alternative, recombination systems.

In order to enable vectors which only contain a single chain to be eliminated and an additional increase in the relative content of recombinant vectors to be obtained as a consequence, the said vector can be arranged to have a selection marker which is initially non-functional and which is rendered functional by the recombination.

Preferably, the selection marker comprises a gene which permits selection, when it is expressed, and a promoter which is specific for the gene, the promoter being inserted into one of the vectors and the marker gene being inserted into the other, in such a way that they become linked in the recombinant vector which is obtained. The preferred markers include the genes, together with their promoters, for resistance to chloramphenicol, to tetracyclines and to gentanycin.

Naturally, the two vectors can also contain specific markers which can be used in the specific construction of each of the vectors, so as to permit or improve selection of each of the vectors during the process of its construction. As an example, these markers can be the genes for resistance to antibiotics such as kanamycin and ampicillin.

Preferably, a thermo-inducible recombinase is used to control the recombination step between the first and the second vector, for example by means of choosing a suitable host such as the E. coli strain D1210 HP, which is to be found in the catalogue of the American company Stratagene.

The invention also relates to the vectors which are obtained by the process according to the invention, in particular the vectors of the plasmid or phagemid type, which are characterized by the presence of a sequence encoding a variable part of an antibody light chain, and a sequence encoding a variable part of an antibody heavy chain, the said sequences. being accompanied, in suitable environments, by elements which enable them to be expressed in a host, the said light-chain and heavy-chain sequences, together with the said means which are linked to them, being respectively separated by unique irreversible integration sites such as, in particular, attP or attB.

Finally, the invention relates to multicombinatorial libraries which are formed by the vectors according to the invention and which combine, in a random manner, a sequence encoding one of the polypeptide types, such as a variable part of a light chain, and a sequence encoding the other polypeptide type, such as a variable part of a heavy chain.

An example will now be described of the construction of a recombinant vector according to the invention which combines the variable parts of the light chain and the heavy chain of one and the same anti-HIV gp160 clone, a vector which is found to be able to express the genes of the said light and heavy variable parts and to present their expression products at its surface or, as a variant, to release them in the form of a heavy chain-light chain combination which recognizes the gp160 antigen.

The same technique can be used to effect multi-combinatorial constructs which link the genes from a repertoire of light-chain variable parts to a gene for a heavy-chain variable part, or a repertoire of heavy-chain variable parts to a gene for a light-chain variable part, or two repertoires of heavy and light variable parts.

FIG. 5 depicts the primers for amplifying pACYC177 SEQ ID NOS. 1 and 2, respectively.

FIG. 6 depicts the sequence of the 30 bp linker SEQ ID NOS. 5 and 4, respectively.

FIG. 7 depicts the oligonucleotide which incorporates the AttB recombination sequence SEQ ID NOS. 5 and 6 respectively.

FIG. 8 depicts the sequence of the 70 bp linker SEQ ID NOS. 7 and 8, respectively.

FIG. 9 depicts the primers for amplifying the lac promoter SEQ ID NOS. 9 and 10, respectively.

FIG. 10 depicts the sequence of the 98 bp linker SEQ ID NOS. 11 and 12, respectively.

FIG. 11 depicts the primers for amplifying the anti-gp 160 $V_L$ chain SEQ ID NOS. 13 and 14, respectively.

FIG. 12 depicts the primers for amplifying pM825 SEQ ID NOS. 15 and 16, respectively.

FIG. 13 depicts the primers for amplifying the gene for resistance to chloramphenicol SEQ ID NOS. 17 and 18, respectively.

FIG. 14 depicts the sequence of the 68 bp linker SEQ ID NOS. 19 and 20, respectively.

FIG. 15 depicts, the sequence of the 115 bp linker SEQ ID NOS. 21 and 22, respectively.

FIG. 16 depicts the primers for amplifying gene III SEQ ID NOS. 23 and 24, respectively.

FIG. 17 depicts the primers for amplifying the anti-gp 160 $V_H$ chain SEQ ID NOS. 25 and 26, respectively.

FIG. 18 depicts the primers for amplifying the AttP recombination sequence SEQ ID NOS. 27 and 28, respectively.

FIG. 19 depicts the primers for amplifying the heavy chain which introduces the amber mutation SEQ ID NOS. 29 and 30, respectively.

FIG. 20 depicts the primers for amplifying the promoter of the gene for resistance to chloramphenicol SEQ ID NOS. 31 and 32, respectively.

Figure 1:
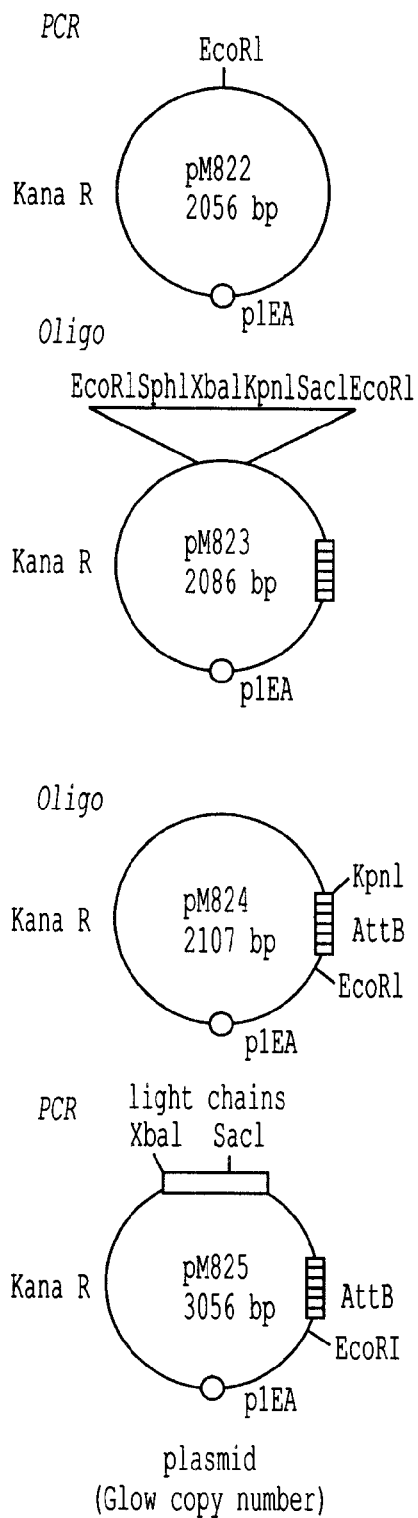
FIG. 1 is a diagrammatic representation of the construction steps starting from pM822 and arriving at pM825.
Figure 2:
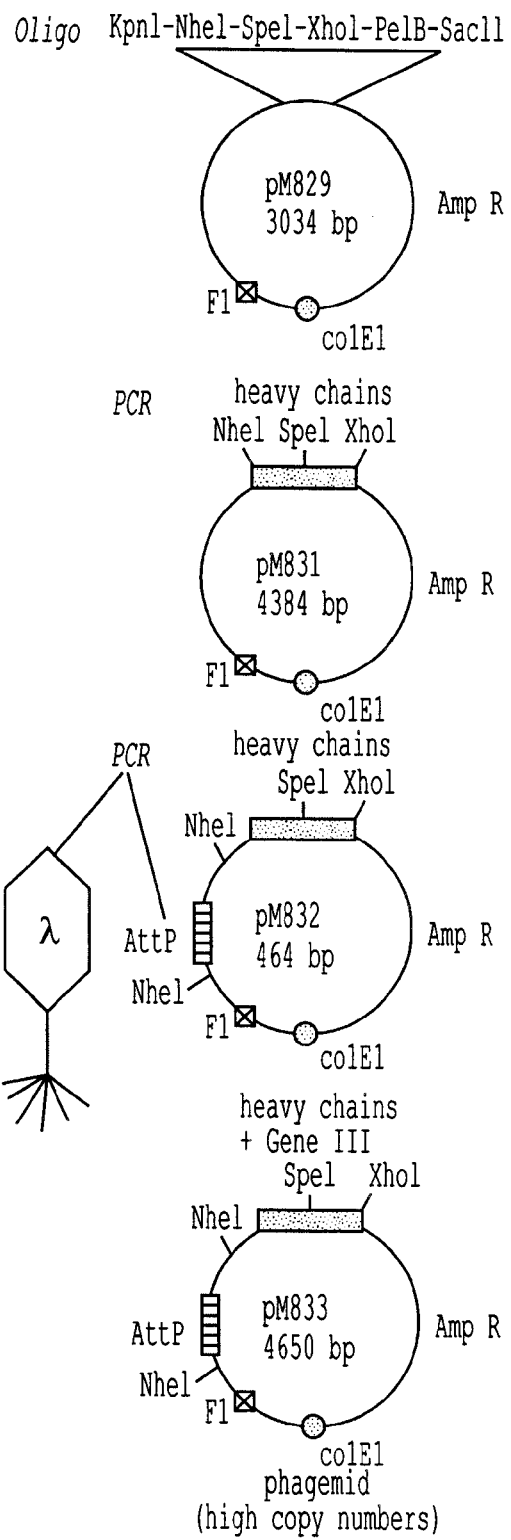
FIG. 2 is a diagrammatic representation of the construction steps starting from pM829 and arriving at pM833.

I—Creation of a plasmid which possesses a p15A origin of replication, a gene for resistance to kanamycin and an AttB recombination sequence for inserting the gene or library of genes for light-chain variable regions.

1) A fragment of 2050 bp, covering bases 759 to 2810, of the plasmid pACYC177 is amplified by PCR (polymerase chain reaction). This plasmid (ATCC 37031), which is distributed by Biolabs, is listed, and its sequence described, in the databases (GenBank accession no. X06402). This amplified fragment encompasses the gene for resistance to kanamycin, including its promoter, the p15A origin of replication and an EcoRI site at each end. The PCR-amplified fragment is then recircularized in order to form a plasmid, designated pM822, of 2056 bp.

The primers which are used for amplifying the fragment are described in FIG. 5 and in the identifiers SEQ ID No. 1 and 2.

2) A synthetic adapter (linker) of 30 bp, encompassing the SacI, KpnI, XbaI and SphI restriction sites, is inserted into the unique EcoRI site of vector pM822, with the resultant vector, of 2086 bp, being designated pM823. The synthetic adapter (linker) primer sequences are given in FIG. 6 and in the identifiers SEQ ID No. 3 and 4.

3) The AttB recombination sequence of 23 bp, in the form of a synthetic oligonucleotide, is inserted into vector pM823 between the SacI and KpnI sites, controlling the 5'–3' orientation by destroying the SacI site by modifying its last base. This results in a plasmid, pM824, of 2107 bp. The synthetic oligonucleotide sequences which correspond to the AttB recombination site are described in FIG. 7 and in the identifiers SEQ ID No. 5 and 6.

4) Insertion of the cassette for cloning the variable parts, $V_L$, of the light chains in order to construct a phagemid, designated pM452, the phagemid pBluescript 11SK+ (marketed by Stratagene) of 2961 bp is digested with the enzymes AflIII and KpnI, and a fragment of 501 bp, encompassing the lactose promoter and various cloning sites, is eliminated. An adapter of 70 bp, which is depicted in FIG. 8, whose primer sequences are described in identifiers SEQ ID No. 7 and 8 encompassing the BglII, NheI, EcoRI, SacI, XbaI and NotI restriction sites, is synthesized and the linker is inserted between AflIII and KpnI in order to arrive at phagemid pM836 of 2530 bp.

A fragment of 171 bp, which is amplified from pBluescript (bases 802 to 973) by PCR using the primers corresponding to sequence identifiers SEQ ID No. 9 and 10 (FIG. 9), with this fragment containing the lac promoter, is inserted between the NheI and EcoRI sites in order to obtain phagemid pM837.

A synthetic adapter of 98 bp, which contains the PelB signal sequence (FIG. 10 and identifiers SEQ ID No. 11 and 12), is inserted between EcoRI and SacI of pM837 in order finally to obtain a phagemid, pM838, of 2795 bp.

The PCR-amplified (cDNA library) 642 bp sequence encoding the $V_L$ region of a light chain of an anti-HIV gp 160 clone is inserted between the SacI and XbaI sites, thereby enabling the reading frame to be conserved between PelB and the light chain. The primers (FIG. 11) are defined in the sequence identifiers SEQ ID No. 13 and 14. The phagemid pM452 (3427 bp) is obtained, which phagemid contains the $V_L$ cassette (lac promoter, PelB signal sequence and the (642 bp)sequence which encodes the light chain of the anti-gp 160 clone).

Phagemid pM452 is digested with Nhe1 and XbaI in order to release a fragment of 960 bp which corresponds to the $V_L$ cassette and which is purified.

This fragment is then inserted into the vector pM824 between the KpnI and XbaI sites while destroying the KpnI site in order to control the orientation, yielding the plasmid pM825 of 3056 bp.

5) A unique AscI site is created 3' of the AttB sequence by amplifying the entire pM825 plasmid by means of PCR using two primers (FIG. 12) possessing an AscI site at their end and having the sequences given in indicators SEQ ID No. 15 and 16. The plasmid which is modified in this way is designated plasmid pM826 (3050 bp).

The gene for resistance to chloramphenicol (770 bp), lacking its promoter, is amplified by PCR from plasmid pBR328 (Boehringer, Genbank Accession VB0004). The amplification is carried out using the primers (FIG. 13) whose sequences are indicated in sequence identifiers SEQ ID No. 17 and 18. The gene for resistance to chloramphenicol is cloned into the AscI site of plasmid pM826, with the correct orientation for its expression being determined, after the recombination step, by means of sequencing. A plasmid designated pM827, of 3816 bp, is thus obtained.

II—Creation of a vector of the phagemid type which carries two, ColE1 and f1, origins of replication, a gene for resistance to ampicillin and an AttP recombination sequence for inserting a library of heavy-chain variable regions.

1) Modification of the pBluescript vector SKII+ (Stratagene, Genbank Accession X52328) in order to obtain a phagemid which is able to present a Fab, which is fused within gene III (surface protein), at its surface:

After having digested the pBluescript with SacI and destroyed the SacI site by the action of mung bean nuclease, and then having digested with KpnI in order to eliminate the multiple cloning site (polylinker) (107 bp), a synthetic adapter of 68 bp (FIG. 14), containing the SacII, XhoI, SpeI, NheI and NotI sites (sequences SEQ ID No. 19 and 20), is inserted, resulting in the phagemid pM828 of 2922 bp.

A synthetic adapter of 115 bp (SEQ ID No. 21 and 22) is created which contains the PelB signal sequence. This linker (FIG. 15) is inserted between the SacII and XhoI sites in order to yield the phagemid pM829 of 3034 bp.

A flexible adapter of 15 bp (FIG. 16 and identifiers SEQ ID No. 23 and 24) and gene III of phage M13 (663 bp), following amplification by PCR of bases 2223 to 2885 of phage M13 mp18 (Biolabs, Genbank Accession X02513), are inserted between the SpeI and NheI sites of pM828, resulting in the phagemid pM830 of 3709 bp.

The heavy chain of an anti-HIV gp 160 clone (cDNA) of 684 bp is amplified by PCR using primers SEQ ID No. 25 and 26 (FIG. 17). This heavy chain is then inserted between the XhoI and SpeI sites of phagemid pM830 in order to give the phagemid pM831 of 4384 bp, with the reading frame between PelB and the heavy chain and between the latter and gene III being conserved.

Figure 3:
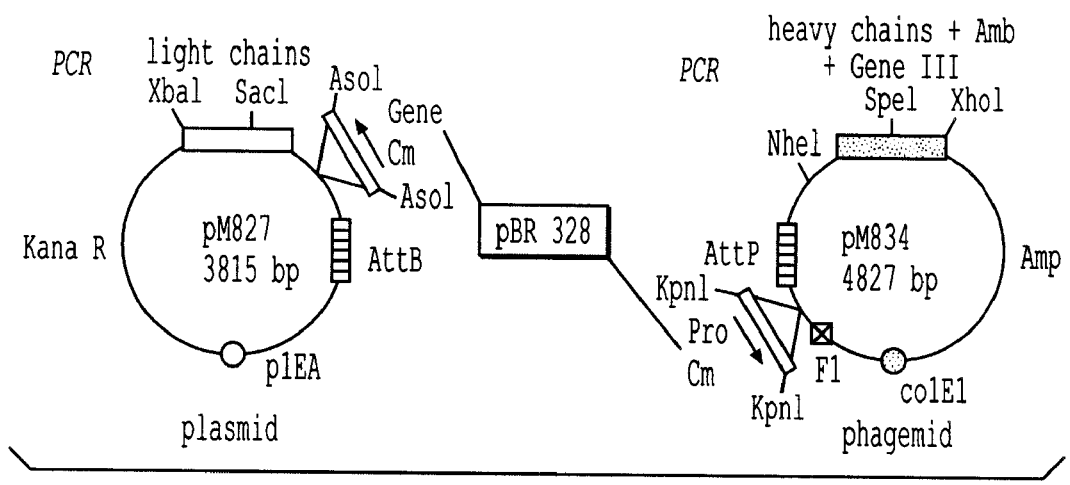
FIG. 3 is a diagrammatic representation of the step for recombining pM827 and pM834.
Figure 4:
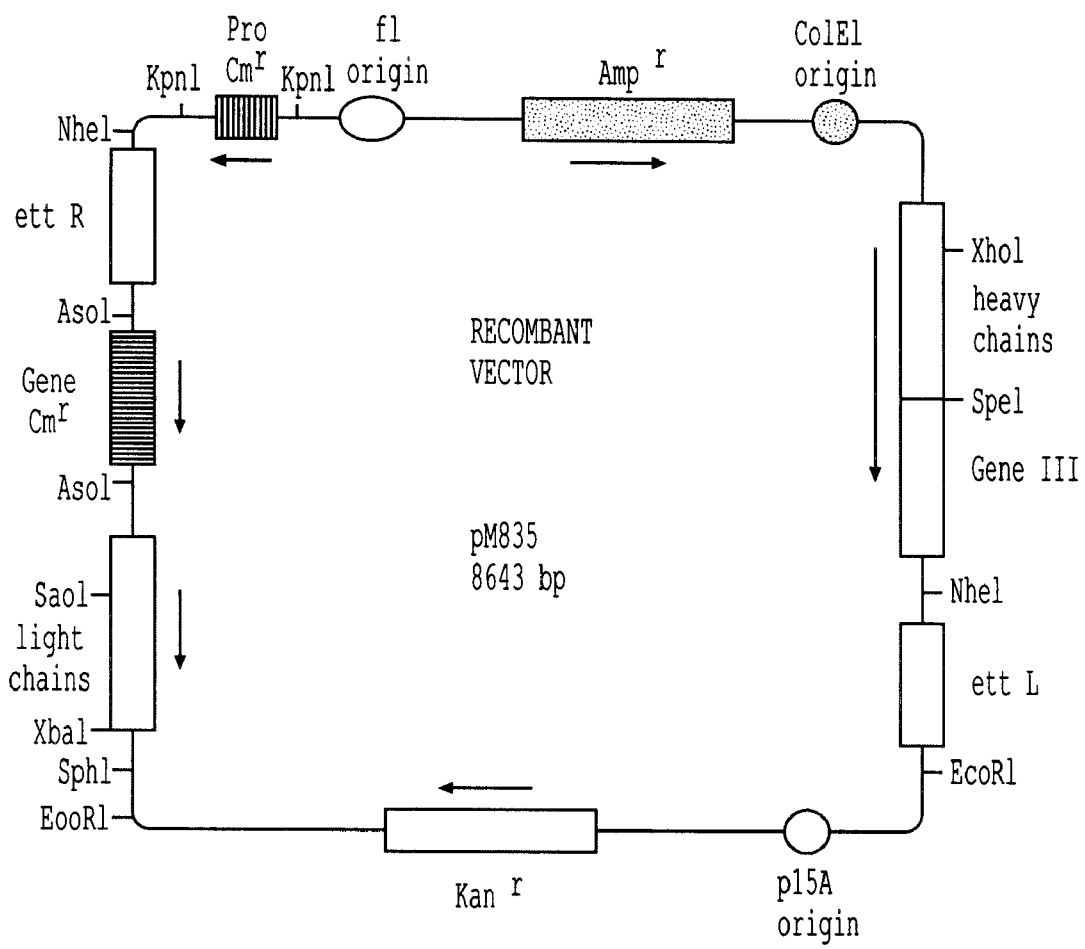
FIG. 4 represents a diagrammatic view of the multicombinatorial vector pM835 which is obtained.

2) Insertion of the AttP recombination sequence of 250 bp within the NheI site following amplification by PCR of bases 27 571 to 27 820 of phage λ (Biolabs, Genbank Accession V00636). The primers which are employed (FIG. 18) possess the sequences SEQ ID No. 27 and 28. The amplified AttP recombination sequence can be inserted in two possible orientations, but only one orientation is retained. This consequently results in the phagemid pM832 of 4641 bp, encompassing the structure depicted in FIG. 3.

3) Modifying the vector for producing soluble Fabs.

For the purpose of readily producing soluble Fabs, an amber mutation (identified as a stop codon in non-suppressing bacterial strains) is thus introduced between the heavy chain and gene III while conserving the reading frame. The heavy chain is amplified by PCR using a 5' primer which possesses the XhoI site (SEQ ID No. 25) and another, 3', primer (SEQ ID No. 29; see FIG. 19) which contains the SpeI site followed by the amber codon TAG and then by the XbaI site, which is compatible with SpeI. The heavy chain is then cloned between the SpeI and XhoI sites of vector pM832, resulting in the phagemid pM833 of 4650 bp.

4) Insertion of the promoter of the gene for resistance to chloramphenicol within the unique KpnI site which is situated 3' of the AttP recombination sequence. One orientation only confers a new resistance on the recombinant vector. The promoter (177 bp) is first amplified by PCR from bases 3270 to 3440 of vector pBR328 (marketed by Biolabs) using primers (FIG. 20) whose sequences are indicated in sequence identifiers SEQ ID No. 30 and 31. The phagemid pM834 of 4827 bp is thus obtained.

III—Recombination between the two vectors pM827 and pM834.

The two aforementioned plasmids serve as the point of departure for obtaining multicombinatorial antibody libraries. In the example which is portrayed, recombination will be carried out between the $V_L$ and $V_H$ chains of the anti-HIV gp 160 clone which is employed. However, if the two vectors are constructed from libraries of genes for antibody heavy chains and/or libraries of genes for antibody light chains, they will enable a multicombinatorial antibody library to be obtained which can then be screened.

When transformed into an appropriate strain (D1210HP), the two vectors will be able to combine with each other due to the AttP and AttB sequences, which are the targets for an inducible int recombination factor. The mechanisms of recombination are described in Chapter 9 of the book "The recombination of genetic material" (Miller H. V., Viral and cellular control of site-specific recombination, 1988, p. 360–384, edited by Brooks Low K., Academic Press). The multicombinatorial vector (8 643 bp) which is thus created possesses three different origins of replication, three antibiotic resistances and the two cassettes for expressing the VL and VH chains.

1) *E. coli* strain D1210HP (distributed by Stratagene), which contains the inducible int recombinase, is transformed, by electroporation, with the F' episome in the form of DNA which is derived from the bacterial strain XL1-Blue (distributed by Stratagene). The bacteria can then be infected with a filamentous phage. The F' episome is maintained in the strain due to its resistance to tetracycline. The transformed strain, D1210HP-F', possesses the following genotype: D1210HP-F': HB101, lacI$^q$, lacY$^+$, λxis$^{31}$ kil$^{31}$ cI857 [F', proAB, lacI$^q$ZΔM15, Tn10(Tet$^R$)].

2) The recombination steps.

This strain is transformed with plasmid pM 827 (containing the $V_L$ chains and resistant to kanamycin), and, in parallel, a compatible strain, for example XL-1 Blue, is transformed with phagemid pM834 (resistant to ampicillin and carrying the VH chains).

Phagemid pM 834 is prepared in the form of phage using the strain which was transformed with it, and the culture of D1210 HP-F', harbouring plasmid pM 827, is then infected at 30° C. (OD=0.6).

After 30 min of infection at 30° C., the culture is subjected to a 42° C. thermal shock for one hour in order to trigger recombination under the influence of the inducible recombinase.

After having returned the culture to 30° C. and added chloramphenicol (final concentration, 50 to 100 μg/ml), the clones are spread on agar medium containing chloramphenicol. One hour later, the helper phage VCSM13 (Kan$^R$), from Stratagene, is added at the rate of $10^{12}$ pfu/100 ml of culture. Then, two hours later, kanamycin is added to 70 μg/ml final concentration and the culture is left for some hours at 30° C.

Analysis of the clones following recombination of vectors pM827 and pM834 demonstrates that combination has taken place successfully. A stable recombinant phagemid, pM835, of 8643 bp, is obtained which expresses a Fab and which is still able to infect strain D1210HP-F. The AttL and AttR junction points were verified by sequencing.

IV—Preparation of a multicombinatorial library from a library of light chains and a library of heavy chains.

The step, I.4, in which the variable region of the light chain of the PCR-amplified anti-HIV gp 160 clone is inserted, is replaced by a similar insertion of the variable regions of the light chains from a library of antibody light chains which is amplified by PCR using a primer system which is known to be suitable and specific for the desired type of light chain, or using a plurality of primer systems if it is desired to carry out the multicombination using populations of different types of light chains. The primer systems for amplifying light chains are well known and described by W. D. Huse et al., Science, Vol 246 (1989), 1275–1281.

In a similar manner, in order to clone the heavy chains, step II.1, for inserting the heavy chain of an anti-HIV gp 160 clone, is replaced by the insertion of a library of heavy-chain variable regions which is amplified by PCR using appropriate primer systems which are described by M. J. Campbell et al., Molecular Immunology, Vol. 29, No. 2 (1992), 193–203 or by W. D. Huse et al above.

Following the recombination steps, the chloramphenicol-resistant clones are selected and are then screened in order to select clones expressing antibody light-chain and heavy-chain combinations which have the desired affinities for the defined antigens, in accordance with the techniques described, for example, by S. F. Parmley et al., in Gene 73 (1988), 305–318.

What is claimed is:

1. A process for producing a multi-combinatorial phagemid library comprising the steps of:

a) providing a first repertoire of genes encoding a population of either type of antibody $V_L$ regions or antibody $V_H$ regions, and b) providing at least one gene encoding a variable region of the other type of $V_L$ regions or $V_H$ regions, or a second repertoire of genes encoding a population of variable regions of the other type of $V_L$ regions or $V_H$ regions;

introducing the genes of the first repertoire into a first vector in order to form a population of vectors carrying different genes of the first repertoire, and introducing the gene encoding the other type of light or heavy antibody chain or the genes of the second repertoire into a second vector, wherein at least one of the vectors, termed recipient, is a phagemid and the vectors respectively contain the E. coli AttB and the phage λ AttP specific recombination sites which are arranged in such a manner as to permit recombination under the influence of the associated recombinase or integrase; and recombining said vectors under the influence of said recombinase or integrase, thereby forming, in a single recombinant vector resulting from the recombination, stable junction sequences and enabling said recombinant vector to contain, in an irreversible manner, a gene of a variable region of either the light or heavy chain antibody types and a gene of the variable region of the other type of light or heavy antibody chain, and to express the two genes in the form of linked polypeptides which are able to appear on the external surface of the product of the said vector, being maintained there and being linked together in a multimeric manner, or simulating a multimer;

wherein the recombinant vector is arranged to have a selection marker which is initially non-functional and which is rendered functional by the recombination.

2. The process according to claim 1, wherein the selection marker comprises a gene which permits selection, when it is expressed, and a promoter which is specific for the gene, the promoter being inserted into either said first or second vectors, and the selection marker being inserted into the other.

3. The process according to claim 2, wherein the marker is the gene for resistance to an antibiotic, together with its promoter.

4. The process according to claim 1, wherein a thermo-inducible recombinase is used to control the step of recombination between the first and the second vectors.

* * * * *

SEQUENCE LISTING

<160> NUMBER OF SEQ ID NOS: 31

<210> SEQ ID NO 1
<211> LENGTH: 26
<212> TYPE: DNA
<213> ORGANISM: Escherichia coli

<400> SEQUENCE: 1
gggaattccc cttaataaga tgatct                                    26

<210> SEQ ID NO 2
<211> LENGTH: 28
<212> TYPE: DNA

```
<213> ORGANISM: Escherichia coli

<400> SEQUENCE: 2
gggaattcca ttcaacaaag ccgccgtc                                28

<210> SEQ ID NO 3
<211> LENGTH: 30
<212> TYPE: DNA
<213> ORGANISM: Escherichia coli

<400> SEQUENCE: 3
aattcgagct cggtacctct agagcatgcg                              30

<210> SEQ ID NO 4
<211> LENGTH: 30
<212> TYPE: DNA
<213> ORGANISM: Escherichia coli

<400> SEQUENCE: 4
aattcgcatg ctctagaggt accgagctcg                              30

<210> SEQ ID NO 5
<211> LENGTH: 27
<212> TYPE: DNA
<213> ORGANISM: Escherichia coli

<400> SEQUENCE: 5
gcctgctttt ttatactaac ttggtac                                 27

<210> SEQ ID NO 6
<211> LENGTH: 27
<212> TYPE: DNA
<213> ORGANISM: Escherichia coli

<400> SEQUENCE: 6
caagttagta taaaaaagca ggcagct                                 27

<210> SEQ ID NO 7
<211> LENGTH: 79
<212> TYPE: DNA
<213> ORGANISM: Escherichia coli

<400> SEQUENCE: 7
catgtgcaga tcttagctag catgaattcc agagctcgtc agttctagag ttaagcggcc    60
gcaatcgagg gggcggtac                                          79

<210> SEQ ID NO 8
<211> LENGTH: 71
<212> TYPE: DNA
<213> ORGANISM: Escherichia coli

<400> SEQUENCE: 8 cgcccctcg attgcggccg cttaactcta gaactgacag actctggaat tcatgctagc    60
taagatctgc a                                                  71

<210> SEQ ID NO 9
<211> LENGTH: 30
<212> TYPE: DNA
<213> ORGANISM: Escherichia coli

<400> SEQUENCE: 9
ctagctagct aacacgacag gtttcccgac                              30
```

<210> SEQ ID NO 10
<211> LENGTH: 26
<212> TYPE: DNA
<213> ORGANISM: Escherichia coli

<400> SEQUENCE: 10
cggaattcgt aatcatggtc atagct                                          26

<210> SEQ ID NO 11
<211> LENGTH: 108
<212> TYPE: DNA
<213> ORGANISM: Escherichia coli

<400> SEQUENCE: 11
aattctaaac tagctagtcg ccaaggagac agtcataatg aaatacctat tgcctacggc     60
agccgctgga ttgttattac tcgctgccca accagccatg gccgagct               108

<210> SEQ ID NO 12
<211> LENGTH: 100
<212> TYPE: DNA
<213> ORGANISM: Escherichia coli

<400> SEQUENCE: 12
cggccatggc tggttgggca gcgagtaata acaatccagc ggctgccgta ggcataggt     60 atttcattat gactgtctcc ttggcgacta gctagtttag                        100

<210> SEQ ID NO 13
<211> LENGTH: 24
<212> TYPE: DNA
<213> ORGANISM: Escherichia coli

<400> SEQUENCE: 13
cagtctgagc tcacgcagcc gccc                                           24

<210> SEQ ID NO 14
<211> LENGTH: 30
<212> TYPE: DNA
<213> ORGANISM: Escherichia coli

<400> SEQUENCE: 14
cgccgtctag aactatgaac attctgtagg                                      30

<210> SEQ ID NO 15
<211> LENGTH: 25
<212> TYPE: DNA
<213> ORGANISM: Escherichia coli

<400> SEQUENCE: 15
ttggcgcgcc tagtaacacg acagg                                           25

<210> SEQ ID NO 16
<211> LENGTH: 25
<212> TYPE: DNA
<213> ORGANISM: Escherichia coli

<400> SEQUENCE: 16
ttggcgcgcc ggtaccaagt tagta                                           25

<210> SEQ ID NO 17
<211> LENGTH: 26
<212> TYPE: DNA

<213> ORGANISM: Escherichia coli

<400> SEQUENCE: 17
ttggcgcgcc gagttatcga gatttt                                26

<210> SEQ ID NO 18
<211> LENGTH: 24
<212> TYPE: DNA
<213> ORGANISM: Escherichia coli

<400> SEQUENCE: 18
ttggcgcgcc attcatccgc ttat                                  24

<210> SEQ ID NO 19
<211> LENGTH: 73
<212> TYPE: DNA
<213> ORGANISM: Escherichia coli

<400> SEQUENCE: 19
tggccaccgc ggtgctcgag gatactagtc agctagctag agagttaagc ggccgcaatc    60
gagggggcgg tac                                              73

<210> SEQ ID NO 20
<211> LENGTH: 69
<212> TYPE: DNA
<213> ORGANISM: Escherichia coli

<400> SEQUENCE: 20 cgcccctcg attgcggccg cttaactctc tagctagctg actagtatcc tcgagcaccg    60
cggtggcca                                                   69

<210> SEQ ID NO 21
<211> LENGTH: 117
<212> TYPE: DNA
<213> ORGANISM: Escherichia coli

<400> SEQUENCE: 21
ggtggcggcc gcaaattcta tttcaaggag acagtcataa tgaaatacct attgcctacg    60
gcagccgctg gattgttatt actcgctgcc caaccagcca tggcccaggt gaactgc      117

<210> SEQ ID NO 22
<211> LENGTH: 123
<212> TYPE: DNA
<213> ORGANISM: Escherichia coli

<400> SEQUENCE: 22
tcgagcagtt cacctgggcc atggctggtt gggcagcgag taataacaat ccagcggctg    60
ccgtaggcaa taggtatttc attatgactg tctccttgaa atagaatttg cggccgccac   120
cgg                                                         123

<210> SEQ ID NO 23
<211> LENGTH: 39
<212> TYPE: DNA
<213> ORGANISM: Escherichia coli

<400> SEQUENCE: 23
ggactagtgg tggcggtggc tctccattcg tttgtgaat                   39

<210> SEQ ID NO 24
<211> LENGTH: 31

```
<212> TYPE: DNA
<213> ORGANISM: Escherichia coli

<400> SEQUENCE: 24
ctagctagca taataacgga atacccaaaa g                                    31

<210> SEQ ID NO 25
<211> LENGTH: 23
<212> TYPE: DNA
<213> ORGANISM: Escherichia coli

<400> SEQUENCE: 25
caggtgcagc tgctcgagtc ggg                                             23

<210> SEQ ID NO 26
<211> LENGTH: 30
<212> TYPE: DNA
<213> ORGANISM: Escherichia coli

<400> SEQUENCE: 26
gcatgtacta gttttgtcac aagatttggg                                      30

<210> SEQ ID NO 27
<211> LENGTH: 30
<212> TYPE: DNA
<213> ORGANISM: Escherichia coli

<400> SEQUENCE: 27
ctagctagcc gcgctaatgc tctgttacag                                      30

<210> SEQ ID NO 28
<211> LENGTH: 29
<212> TYPE: DNA
<213> ORGANISM: Escherichia coli

<400> SEQUENCE: 28
ctagctagca tcaaataatg attttattt                                       29

<210> SEQ ID NO 29
<211> LENGTH: 33
<212> TYPE: DNA
<213> ORGANISM: Escherichia coli

<400> SEQUENCE: 29
gctctagact aactagtttt gtcacaagat ttg                                  33

<210> SEQ ID NO 30
<211> LENGTH: 24
<212> TYPE: DNA
<213> ORGANISM: Escherichia coli

<400> SEQUENCE: 30
ggggtaccga ataaatacct gtga                                            24

<210> SEQ ID NO 31
<211> LENGTH: 25
<212> TYPE: DNA
<213> ORGANISM: Escherichia coli

<400> SEQUENCE: 31
ggggtaccaa aaatacgcc cggta                                            25
```